(12) United States Patent
Rioux et al.

(10) Patent No.: US 6,929,663 B2
(45) Date of Patent: Aug. 16, 2005

(54) LONGITUDINALLY EXPANDING MEDICAL DEVICE

(75) Inventors: Robert Rioux, Ashland, MA (US); Ken Daignault, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 175 days.

(21) Appl. No.: 10/400,200

(22) Filed: Mar. 26, 2003

(65) Prior Publication Data

US 2004/0193283 A1 Sep. 30, 2004

(51) Int. Cl.⁷ .............................. A61F 2/04; A61F 11/00; A61F 2/00; A61M 5/00
(52) U.S. Cl. .................... 623/23.64; 606/108; 606/198; 604/8; 604/106; 600/29
(58) Field of Search ........................... 623/23.64, 23.65, 623/23.66, 23.67, 23.7, 1.13, 1.15; 606/108, 198; 604/106, 107, 8; 600/29

(56) References Cited

U.S. PATENT DOCUMENTS

| | | | |
|---|---|---|---|
| 4,221,457 A | | 9/1980 | Allen et al. |
| 4,222,384 A | | 9/1980 | Birtwell |
| 4,307,723 A | | 12/1981 | Finney |
| 4,432,737 A | | 2/1984 | Johansson |
| 4,432,757 A | | 2/1984 | Davis, Jr. |
| 4,501,580 A | | 2/1985 | Glassman |
| 4,512,338 A | | 4/1985 | Balko et al. |
| 4,553,959 A | | 11/1985 | Hickey et al. |
| 4,592,341 A | * | 6/1986 | Omagari et al. ............ 600/104 |
| 4,655,771 A | | 4/1987 | Wallsten |
| 4,660,560 A | | 4/1987 | Klein |
| 4,699,611 A | * | 10/1987 | Bowden ..................... 606/191 |
| 4,713,049 A | | 12/1987 | Carter |

(Continued)

FOREIGN PATENT DOCUMENTS

| | | |
|---|---|---|
| EP | 0 789 602 B1 | 8/1997 |
| EP | 0 935 977 A3 | 8/1999 |
| EP | 0 943 299 A1 | 9/1999 |
| WO | WO 91/16005 | 10/1991 |
| WO | 96/11721 | 4/1996 |
| WO | WO 99/23952 | 5/1999 |

OTHER PUBLICATIONS

International Search Report for International Patent Application No. PCT/US2004/009379, dated Aug. 25, 2004, 6 pages.

Duerig et al.; "An Overview of Superelastic Stent Design"; Min. Invas. Ther. & Allied Technol. 2000: vol. 9, Issue (3/4), (pp. 235–246).

*Primary Examiner*—Alvin J. Stewart
(74) *Attorney, Agent, or Firm*—Edwards & Angell, LLP

(57) ABSTRACT

A stent for maintaining an open passageway through a body lumen, such as the prostatic urethra of a male patient, includes an elongated segment including a flexible polymer material bridging a plurality of hoops. The elongated segment defines a lumen extending therethrough and has a distal end. A retention structure may be coupled to the distal end of the elongated segment to inhibit the distal end from migrating when the stent is placed within a body of a patient. The flexible polymer material is disposed between the plurality of hoops, thereby creating hinged members that allow for the spaces between the hoops to expand and contract longitudinally to accommodate prostatic swelling when the stent is placed within the prostatic urethra of the patient. A plurality of ridges is disposed along the elongated segment at locations where the flexible material circumscribes the hoops, and these inhibit migration of the stent and facilitate longitudinal expansion by frictionally engaging adjacent tissue, such as the inner wall of the prostatic urethra.

7 Claims, 7 Drawing Sheets

U.S. PATENT DOCUMENTS

| | | |
|---|---|---|
| 4,732,152 A | 3/1988 | Wallsten et al. |
| 4,795,458 A | 1/1989 | Regan |
| 4,798,606 A | 1/1989 | Pinchuk |
| 4,800,882 A | 1/1989 | Gianturco |
| 4,813,429 A | 3/1989 | Eshel et al. |
| 4,813,925 A | 3/1989 | Anderson, Jr. et al. |
| 4,813,935 A | 3/1989 | Haber et al. |
| 4,861,337 A | 8/1989 | George |
| 4,889,137 A | 12/1989 | Kolobow |
| 4,893,623 A | 1/1990 | Rosenbluth |
| 4,907,336 A | 3/1990 | Gianturco |
| 4,911,716 A | 3/1990 | Blom et al. |
| 4,931,037 A | 6/1990 | Wetterman |
| 4,954,126 A | 9/1990 | Wallsten |
| 4,955,859 A | 9/1990 | Zilber |
| 4,973,301 A | 11/1990 | Nissenkorn |
| 4,985,022 A | 1/1991 | Fearnot et al. |
| 4,990,155 A | 2/1991 | Wilkoff |
| 4,994,066 A | 2/1991 | Voss |
| 4,995,868 A | 2/1991 | Brazier |
| 5,002,558 A | 3/1991 | Klein et al. |
| 5,007,868 A | 4/1991 | Fry |
| 5,019,090 A | 5/1991 | Pinchuk |
| 5,026,377 A | 6/1991 | Burton et al. |
| 5,030,227 A | 7/1991 | Rosenbluth et al. |
| 5,041,092 A | 8/1991 | Barwick |
| 5,059,169 A | 10/1991 | Zilber |
| 5,061,275 A | 10/1991 | Wallsten et al. |
| 5,064,435 A | 11/1991 | Porter |
| 5,071,407 A | 12/1991 | Termin et al. |
| 5,078,720 A | 1/1992 | Burton et al. |
| 5,078,736 A | 1/1992 | Behl |
| 5,085,629 A | 2/1992 | Goldberg et al. |
| 5,092,877 A | 3/1992 | Pinchuk |
| 5,116,309 A | 5/1992 | Coll |
| 5,147,370 A | 9/1992 | McNamara et al. |
| 5,167,614 A | 12/1992 | Tessmann et al. |
| 5,176,625 A | 1/1993 | Brisson |
| 5,176,626 A | 1/1993 | Soehendra |
| 5,178,148 A | 1/1993 | Lacoste et al. |
| 5,183,085 A | 2/1993 | Timmermans |
| 5,220,927 A | 6/1993 | Astrahan et al. |
| 5,221,261 A | 6/1993 | Termin et al. |
| 5,222,949 A | 6/1993 | Kaldany |
| 5,224,953 A | 7/1993 | Morgentaler |
| 5,226,913 A | 7/1993 | Pinchuk |
| 5,226,979 A | 7/1993 | Thoma |
| 5,234,457 A | 8/1993 | Andersen |
| 5,246,445 A | 9/1993 | Yachia et al. |
| 5,269,802 A | 12/1993 | Garber |
| 5,282,860 A | 2/1994 | Matsuno et al. |
| 5,300,022 A | 4/1994 | Klapper et al. |
| 5,306,241 A | 4/1994 | Samples |
| 5,312,430 A | 5/1994 | Rosenbluth et al. |
| 5,318,012 A * | 6/1994 | Wilk .......................... 600/205 |
| 5,322,501 A | 6/1994 | Mahmud-Durrani |
| 5,352,198 A | 10/1994 | Goldenberg et al. |
| 5,354,309 A | 10/1994 | Schnepp-Pesch et al. |
| 5,356,423 A | 10/1994 | Tihon et al. |
| 5,372,600 A | 12/1994 | Beyar et al. |
| 5,383,928 A | 1/1995 | Scott et al. |
| 5,391,196 A | 2/1995 | Devonec |
| 5,441,516 A | 8/1995 | Wang et al. |
| 5,472,435 A | 12/1995 | Sutton |
| 5,476,505 A | 12/1995 | Limon |
| 5,496,277 A | 3/1996 | Termin et al. |
| 5,500,013 A | 3/1996 | Buscemi et al. |
| 5,514,176 A | 5/1996 | Bosley, Jr. |
| 5,514,178 A | 5/1996 | Torchio |
| 5,518,498 A | 5/1996 | Lindenberg et al. |
| 5,520,697 A | 5/1996 | Lindenberg et al. |
| 5,527,337 A | 6/1996 | Stack et al. |
| 5,531,741 A | 7/1996 | Barbacci |
| 5,540,713 A | 7/1996 | Schnepp-Pesch et al. |
| 5,554,181 A | 9/1996 | Das |
| 5,562,641 A | 10/1996 | Flomenblit et al. |
| 5,599,291 A | 2/1997 | Balbierz et al. |
| 5,601,591 A | 2/1997 | Edwards et al. |
| 5,662,700 A * | 9/1997 | Lazarus ...................... 606/194 |
| 5,667,486 A | 9/1997 | Mikulich et al. |
| 5,766,209 A * | 6/1998 | Devonec ........................ 604/8 |
| 5,776,161 A | 7/1998 | Globerman |
| 5,795,319 A | 8/1998 | Ali |
| 5,830,179 A | 11/1998 | Mikus et al. |
| 5,833,707 A | 11/1998 | McIntyre et al. |
| 5,843,166 A | 12/1998 | Lentz et al. |
| 5,916,195 A | 6/1999 | Eshel et al. |
| 5,964,744 A | 10/1999 | Balbierz et al. |
| 6,033,413 A | 3/2000 | Mikus et al. |
| 6,039,755 A | 3/2000 | Edwin et al. |
| 6,673,042 B1 * | 1/2004 | Samson et al. ............. 604/104 |
| 6,773,457 B2 * | 8/2004 | Ivancev et al. ............ 623/1.28 |
| 2001/0047164 A1 | 11/2001 | Teague et al. |
| 2001/0053936 A1 | 12/2001 | Whitmore, III |
| 2002/0055787 A1 | 5/2002 | Lennox et al. |
| 2002/0065476 A1 | 5/2002 | Whalen et al. |
| 2002/0107540 A1 | 8/2002 | Whalen et al. |
| 2002/0173741 A1 | 11/2002 | Rioux et al. |
| 2002/0177902 A1 | 11/2002 | Rioux et al. |
| 2002/0183852 A1 | 12/2002 | McWeeney |
| 2003/0040803 A1 * | 2/2003 | Rioux et al. ............... 623/23.7 |
| 2004/0215322 A1 * | 10/2004 | Kerr .......................... 623/1.13 |

* cited by examiner

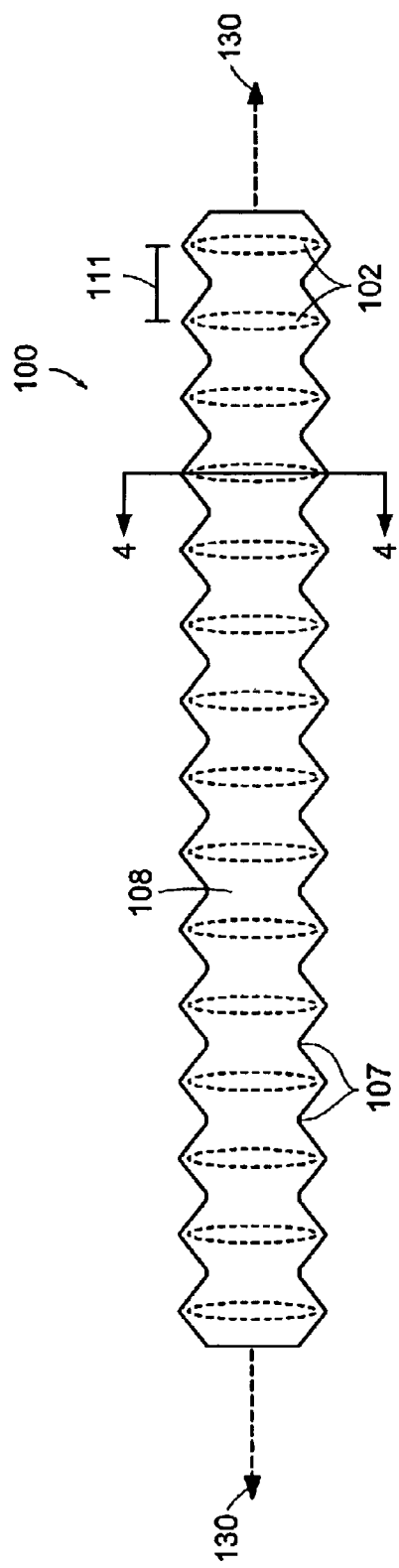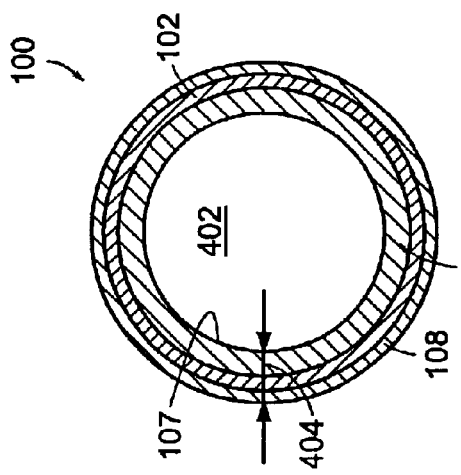

LONGITUDINALLY EXPANDING MEDICAL DEVICE

TECHNICAL FIELD

This invention generally relates to medical devices and maintaining a body passageway open.

BACKGROUND INFORMATION

Stents have been employed, for example, in the urethra, the ureters, the biliary tract, the cervix, the rectum, the esophagus, and blood vessels of mammals to relieve the pathological effects of constrictions or obstructions occurring in these passageways.

Bladder obstruction arising from enlargement of the prostate gland in males is one of the most commonly encountered disorders in urology. The prostate gland lies under the bladder and surrounds the passageway known as the prostatic urethra, which transfers fluids from the bladder to the sphincter and ultimately through the rest of the urethra and outside the body. An enlarged prostate gland constricts the prostatic urethra leading to a condition known as benign prostatic hyperplasia ("BPH"). BPH causes a variety of obstructive symptoms, including urinary hesitancy, straining to void, decreased size and force of the urinary stream, and in extreme cases, complete urinary retention possibly leading to renal failure. A number of other irritating symptoms also may accompany BPH, including urinary frequency and urgency, nocturnal incontinence, and extreme discomfort.

SUMMARY OF THE INVENTION

Existing stents are unable to change their length to accommodate prostatic swelling. As a result, the patient may continue to experience symptoms associated with BPH. Indeed, during severe swelling of the prostate, such as, for example, after "thermal effect treatment" of an enlarged prostate, the bladder-end of the stent may become occluded by surrounding tissue. Consequently, the flow of urine through the stent is reduced, if not completely obstructed. Moreover, some stents, such as wire mesh stents, may become entangled with prostate tissue leading to infection and discomfort. Under such conditions, prostate tissue often penetrates the perforations of the wire mesh stent rendering it difficult, if not impossible, to remove without surgical intervention.

Also, internal forces from involuntary bodily functions (such as peristalsis and other secretory forces, as well as patient movement) may force some stents out of their intended position within the prostatic urethra. For instance, the bladder can exert intense pressure during urination, which tends to expel a stent positioned within the prostatic urethra. It is also possible that normal body motions, such as walking or running, may displace a stent at this location.

It is an object of the invention to maintain an open passageway through the patient's prostatic urethra, while also allowing the stent to expand longitudinally to accommodate prostatic swelling. It is another object of the invention to provide the patient with a stent that is resistant to ingrowth of tissue and is also resistant to migration once positioned within the patient's urinary system.

Generally, the medical device of the present invention includes a series of hoops surrounded by a flexible material defining a lumen therethrough. Similar to the bellows of an accordion, the flexible material collapses between adjacent hoops, forming a series of hinged members. Generally, longitudinal expansion is provided by the hinged members disposed between the hoops, and in-growth of tissue is prevented by the flexible material that bridges or otherwise encapsulates the hoops. The flexible material also forms a plurality of ridges at the locations where the flexible material circumscribes the hoops. These ridges inhibit migration of the stent through the prostatic urethra by engaging the adjacent tissue as the swelling prostate exerts lateral pressure on the stent. The swelling prostate also frictionally engages the ridges, which facilitates longitudinal expansion by pushing and forcing the hoops apart.

To further inhibit the migration of the stent, a multi-winged malecot or other radially expanding retention structure can be attached to a bladder-end of the stent to inhibit the stent from migrating out of the bladder. The malecot includes two or more wings that are collapsible to allow for passage of the prostatic stent into and through the urethra of the patient and expandable once located in the bladder. The multi-winged malecot can be biased in an extended configuration, such that the multi-winged malecot will return to the extended configuration in the absence of external forces acting upon the malecot.

The directional terms proximal and distal require a point of reference. As used herein, the point of reference is from the perspective of a medical professional. Therefore, the term distal refers to a direction that points into the body of the patient and away from the medical professional, whereas the term proximal refers to a direction that points out of the patient's body.

In one aspect, the invention is directed to a medical device for use in a body of a patient including an elongated segment including a plurality of hoops defining a lumen therethrough. The medical device further includes a flexible polymer material bridging the plurality of hoops that allows the elongated segment to expand and contract. In some embodiments of the foregoing aspect of the invention, each of the plurality of hoops comprises a wire. In another embodiment, at least one of the wires includes a biocompatible material that includes stainless steel, titanium, a nickel-titanium alloy, or a polymer. Each of the hoops is spaced apart from at least one other of the hoops, in another embodiment. In still another embodiment, the flexible polymer material is disposed between the plurality of hoops, allowing the spaces between the plurality of hoops to expand and contract to accommodate prostatic swelling when the device is within the prostatic urethra of the patient. The flexible polymer material may include a low durometer silicone. In another embodiment, the flexible polymer is resilient.

In some embodiments of the foregoing aspect of the invention, the medical device includes a retention structure to inhibit migration of the device. The retention structure extends from a first end of the elongated segment and may include a coiled shape, a J-curl, a barb, or a malecot. In one embodiment, the coiled shape is selected from the group consisting of conical, spherical, helical, frusto-conical, and combinations thereof. In some embodiments, the elongated segment includes a second retention structure to inhibit migration of the device. The second retention structure extends from a second end of the elongated segment that is opposite the first end. The second retention structure may include a coiled shape, a J-curl, a barb, or a malecot. In one embodiment, the coiled shape is selected from the group consisting of conical, spherical, helical, frusto-conical, and combinations thereof.

In another aspect, the invention relates to a stent for use in a prostatic urethra of a patient including an elongated segment including a first end, a second end, a plurality of hoops defining a lumen therethrough, and a flexible polymer material bridging the plurality of hoops to facilitate expansion of the elongated segment during prostatic swelling when the stent is within the prostatic urethra of the patient. The stent also includes a first malecot comprising a proximal end and a distal end. The proximal end of the first malecot can be disposed at the first end of the elongated segment and a curved tip can be disposed at the distal end of the first malecot. The stent can further include a second malecot disposed at the second end of the elongated segment.

In some embodiments of the forgoing aspect of the invention, each of the plurality of hoops includes a wire. In one embodiment, at least one of the wires includes a biocompatible material that includes stainless steel, titanium, a nickel-titanium alloy, or a polymer. In one embodiment, each of the hoops is spaced apart from at least one other of the hoops. The flexible polymer material includes a low durometer silicone in one embodiment. In another embodiment, the flexible polymer material is resilient.

In yet another aspect, the invention is directed to a method of placing a stent in a prostatic urethra of a patient. The method includes the steps of providing a stent and inserting the stent into the prostatic urethra of the patient. The stent includes an elongated segment, including a plurality of hoops defining a lumen therethrough, and a flexible polymer material bridging the plurality of hoops that allows spaces between the plurality of hoops to expand and contract to accommodate swelling of a prostate when the stent is within the prostatic urethra of the patient. In an embodiment of the foregoing aspect of the invention, the stent includes a retention structure to inhibit migration of the stent. The retention structure extends from a first end of the elongated segment. In another embodiment, the inserting step includes positioning the retention structure into a bladder of the patient.

BRIEF DESCRIPTION OF THE DRAWINGS

In the drawings, like reference characters generally refer to the same parts throughout the different views. Also, the drawings are not necessarily to scale, emphasis generally being placed upon illustrating the principles of the invention. In the following description, various embodiments of the present invention are described with reference to the following drawings, in which:

FIG. 3 shows a schematic side view of the stent of FIG. 2 in an expanded configuration;

FIG. 4 is a schematic transverse cross-sectional view of the stent of FIG. 3 taken at line 4—4;

DESCRIPTION

Embodiments of the present invention are described below. The invention is not limited, however, to these embodiments. For example, various embodiments of the invention are described in terms of a urethral stent; however, embodiments of the invention may be used in one or more other lumens within a body, such as the ureter, for example.

Figure 1:
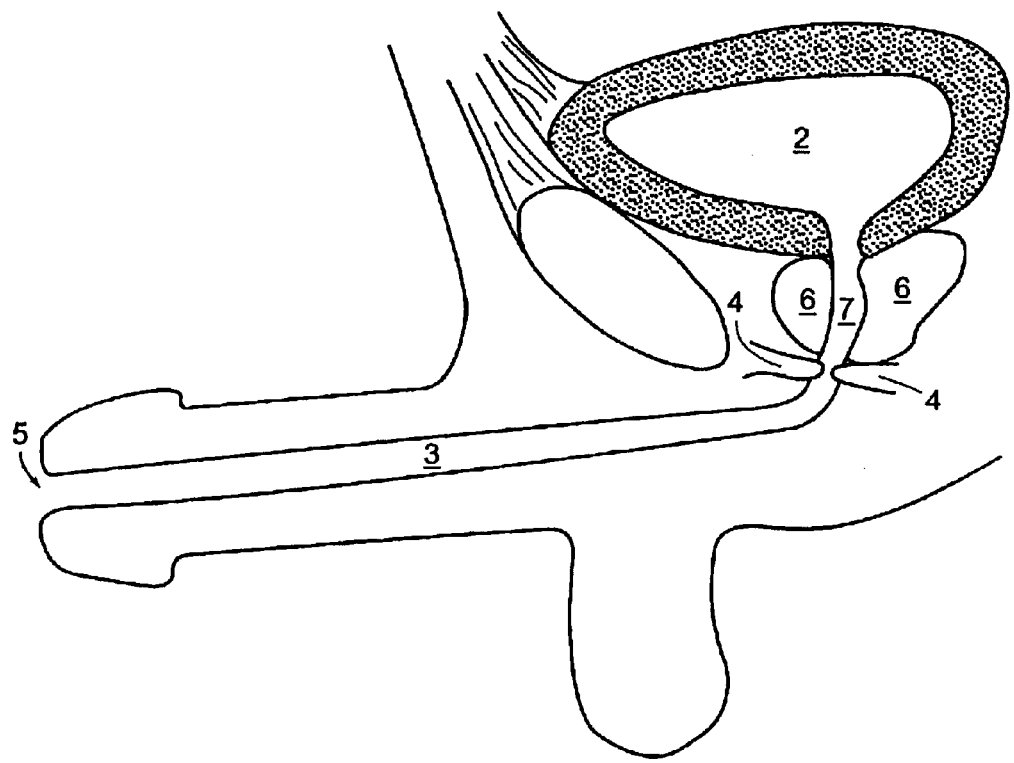
FIG. 1 is a schematic view of the male urinary system.

Urine retention and reduced urination are two common symptoms that some male patients afflicted with benign prostatic hyperplasia (BPH) endure. BPH is a medical condition in which a patient's prostate enlarges due to disease or decreasing hormone production. FIG. 1 illustrates a typical male urinary system 1. The system 1 includes a bladder 2, a urethra 3, a sphincter 4, a meatus 5, and a prostate 6. The prostate 6 is a male reproductive organ that surrounds a section of the urethra 3 generally known as the prostatic urethra 7. Due to the prostate's location, the male urinary system 1 may be constricted and thus obstructed when the patient's prostate 6 enlarges. Stents in accordance with the invention will maintain an open passageway through the prostatic urethra 7 and expand longitudinally to accommodate swelling of the prostate 6.

Figure 2:
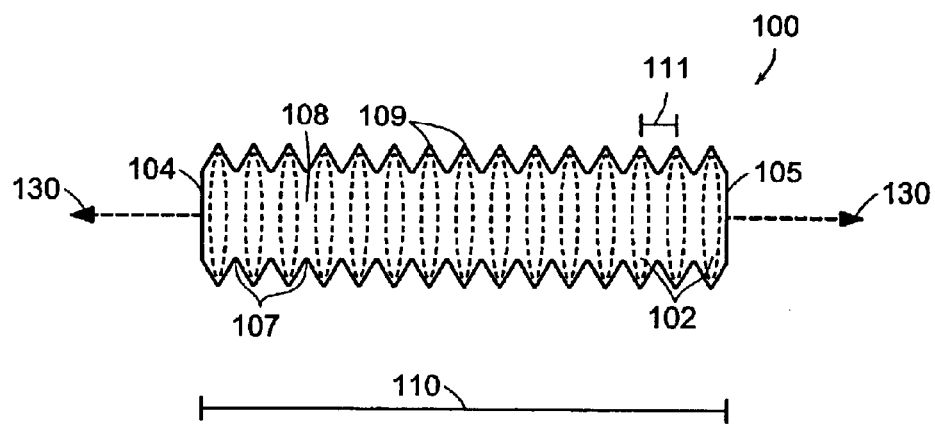
FIG. 2 is a schematic side view of an embodiment of a longitudinally expanding stent in accordance with the invention in a compact configuration.

FIG. 2 illustrates the general structure of one embodiment of the invention. FIG. 2 depicts a stent 100 including an elongated segment 110 with a plurality of individual hoops 102 disposed therein. In a particular embodiment, the hoops 102 are oriented substantially perpendicular to the longitudinal axis 130 of the stent 100 (See also FIG. 6). Each of the plurality of hoops 102 may be made from an element that can be circularized, such as, for example, a stainless steel wire. Alternatively, a wire of any biocompatible material, such as, for example, a polymer, titanium, or a nickel-titanium alloy may be used. Examples of polymers include nylon based biocompatible polymers, polytetrafluoroethylene, silicone, polyurethane, polyethylene, and thermoplastic elastomers.

The wire used to form each of the hoops 102 may have one of a variety of cross-sectional shapes, such as, for example, circular, square, rectangular, triangular, or trapezoidal. In a particular embodiment, the wire has a circular cross-sectional shape having a cross-sectional area defined by the wire's diameter. The diameter or thickness, or more generally the cross-sectional area or shape of the wire selected for the hoops 102 influences the radial strength of the stent 100. Thus, the diameter of the wire selected needs to be sufficiently large to assure that proper radial strength of the stent 100 is achieved to prevent against obstruction of the patient's prostatic urethra 7 resulting from the constriction created by the patient's enlarged prostate 6. The diameter of the wire used to form the plurality of hoops 102 is generally in the range of from about 0.1 mm to about 3 mm, which corresponds to a cross-sectional area in the range of about $7.9 \times 10^{-3}$ mm$^2$ to about 7.1 mm$^2$. In a particular embodiment, the wire's diameter is 1 mm, which corresponds to a cross-sectional area of about 0.8 mm$^2$.

The elongated segment 110 also includes a flexible polymer material 108 that bridges or connects the plurality of hoops 102 forming a lumen therethrough. Alternatively, the hoops 102 can be embedded within the flexible polymer material 108. In a particular embodiment, the flexible polymer material 108 encapsulates or forms a sheath around the plurality of hoops 102 (See, e.g., FIG. 6). The flexible polymer material 108 is a non-porous membrane that inhibits in-growth of body tissue around the plurality of hoops 102 and into the lumen 402, thereby preventing encrustation of the prostatic stent 100. The flexible polymer material 108 may be constructed of a biocompatible plastic such as, but not limited to, any polyester, nylon based biocompatible polymers, polytetrafluoroethylene, silicone, polyurethane, polyethylene, and thermoplastic elastomers. In some embodiments, the flexible polymer material 108 may be made from silicone having a hardness in the general range of about 0 to 80 on the Shore A durometer scale. In a particular embodiment, the flexible polymer material 108 is made from silicone having a hardness of about 10 on the Shore A durometer scale.

The shape of the flexible polymer material 108 allows the stent 100 to expand longitudinally in response to prostatic swelling. The flexible polymer material 108 is collapsed between adjacent hoops 102 forming a plurality of hinged members 107 disposed along the length of the elongated segment 110. The stent 100 also has a plurality of ridges 109 disposed between adjacent hinged members 107. Both the hinged members 107 and the ridges 109 encircle the lumen 402 substantially perpendicular to a longitudinal axis 130 of the elongated segment 110, thereby forming an expandable bellows-like structure. The hoops 102 are arranged such that each hoop 102 is seated within a ridge 109, thus securing the plurality of hoops 102 within the flexible polymer material 108. In operation, the plurality of hinged members 107 allow the stent 100 to expand along a longitudinal axis 130 of the elongated segment 110, as shown in FIG. 3. In one embodiment, the flexible polymer material 108 is resilient, allowing the stent 100 to regain its original shape after being deformed.

The elongated segment 110 may be manufactured by various methods. In one method, the flexible polymer material 108 is produced by dipping an open-ended preform having a lumen extending therethrough and a shape substantially equivalent to the shape of the elongated segment 110 into a molten bath of silicone or other biocompatible polymer. The formed flexible polymer material 108 may then be removed from within the lumen of the preform and manually loaded with the hoops 102 using, for example, tweezers. The hoops 102 are inserted into the lumen 402 of the flexible polymer material 108 such that each hoop 102 is seated within a ridge 109 (See FIG. 2). In an alternative method, the prostatic stent 100 may be manufactured using a bellows-shaped deformable mandrel with a plurality of hoops 102 disposed around the ridges of the bellows. The mandrel is dipped into a molten bath of silicone to create the elongated segment 110 including the formed flexible polymer material 108 with hinged members 107 and ridges 109 and the plurality of hoops 102 seated therein. The flexible polymer material 108 is subsequently removed by deforming the mandrel and disengaging the elongated segment 110. In a further alternative method, the stent 100 may be manufactured using liquid injection molding techniques, wherein the hoops 102 are properly arranged in a closed mold having a lumen extending therethrough and a shape substantially equivalent to the shape of the elongated segment 110. A liquid silicone, for example, is subsequently injected into the mold, thereby embedding the hoops into a flexible lumen in accordance with the invention.

The diameter of the elongated segment 110 is between about 16 French to about 22 French, preferably about 18 French to about 21 French, depending on the size of the patient. The length of the stent 100 may vary to suit the individual needs of particular patients. For example, the length of the stent 100 in the compact configuration may be between about 2.5 cm to about 8.3 cm depending on the size of the patient's prostatic urethra 7, which varies in length from about 1.5 cm to about 7.6 cm. To determine the length of the patient's prostatic urethra 7, a conventional measuring catheter can be employed. By varying the diameter and length of the segments, the stent 100 may be tailored to the individual needs of particular patients.

FIG. 3 is a schematic side view of the stent 100 of FIG. 2 illustrating the expanded configuration. During longitudinal expansion, the hinged members 107 assume an open configuration, thus increasing a distance 111 between adjacent hoops 102. As a result, the stent 100 assumes an expanded configuration, as represented in FIG. 3. Because the plurality of hoops 102 are unconnected, the amount of longitudinal expansion is limited only by the construction of the flexible polymer material 108. In one embodiment the distance 111 is between about 3 mm to about 6 mm, preferably about 4 mm to about 5 mm, with the flexible polymer material 108 in a neutral configuration, i.e., neither compacted nor expanded. The range of expansion for the distance 111 (i.e., from the compacted configuration to the expanded configuration) is about 1 mm to about 12 mm, preferably about 2 mm to about 10 mm. The degree of expansion can be adjusted by, for example, varying a distance 404 that the hinged member 107 extends into the lumen 402 (See FIG. 4). The distance 404 depends on the outside diameter of the stent 100 and the desired range of expansion and should be designed such that the inside diameter of the lumen 402 is about 2 mm to about 6 mm, preferably about 3 mm to about 5 mm. The actual dimensions may be varied to suit a particular application. Also, longitudinal expansion may be adjusted by varying the elasticity of the flexible polymer material 108. The plurality of hinged members 107 may be biased in a compact configuration, as represented in FIG. 2.

FIG. 4 depicts a transverse cross-sectional view of the stent 100 taken at line 4—4 of FIG. 3. FIG. 4 is an enlarged view of stent 100 and depicts a hoop 102, the flexible polymer material 108, and the lumen 402. The flexible polymer material 108' visible on the interior of the stent 100 creates the hinged member 107. The distance 404 represents a measure of how far the hinged member 107 extends into the lumen 402. In some embodiments, the cross-sectional configurations of the lumen 402 can be circular, elliptical, polygonal, wedge-shaped, or combinations thereof.

To inhibit migration of the stent 100, the elongated segment 110 may include retention structures coupled to a proximal end 104 and/or a distal end 105 of the stent 100. To prevent proximal migration of the stent 100 (e.g., down out of the bladder 2 and out of the patient's urinary system) retention structures, such as, for example, a coiled shape, a J-curl, a barb, or a malecot may be coupled to the distal end 105 of the elongated segment 110. A detailed embodiment of a stent 500 including a retention structure is shown in FIGS. 5–7.

Figure 5A:
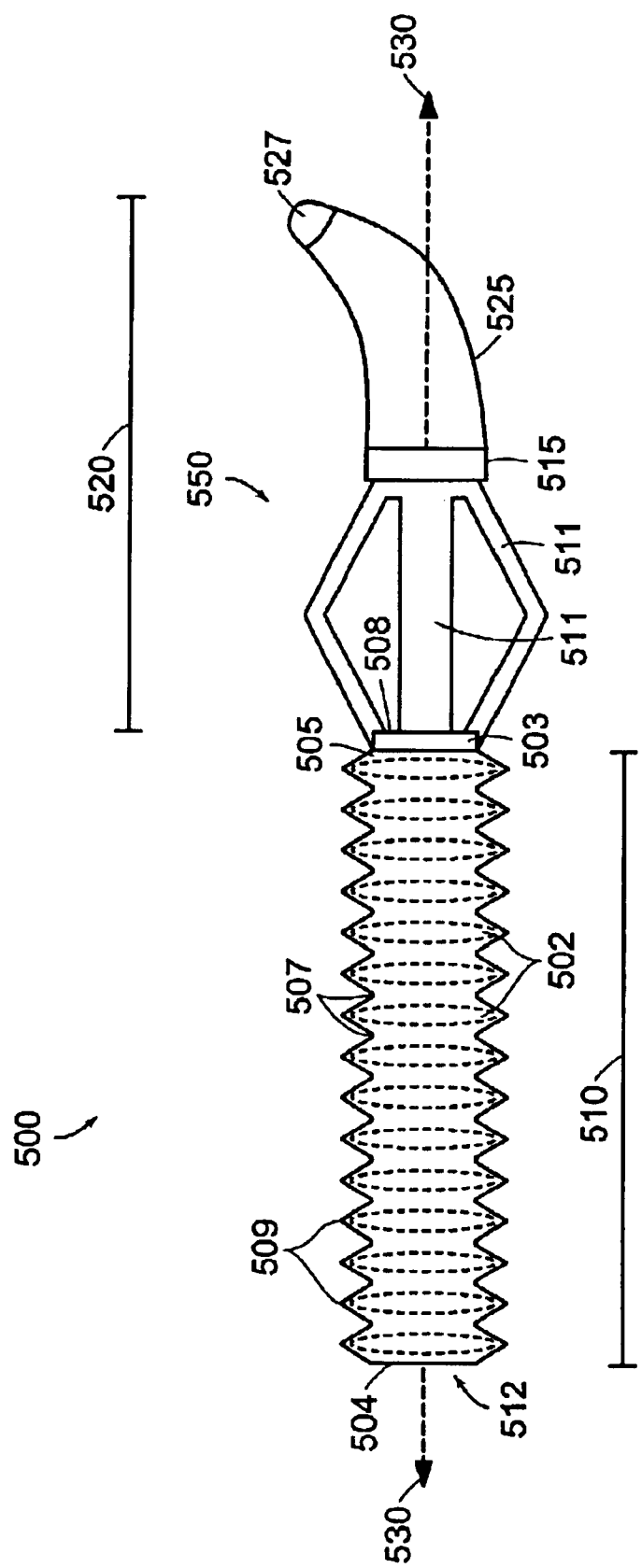
FIGS. 5A and 5B are schematic side views of an alternative stent in accordance with the invention showing a retention structure in a collapsed configuration and an extended configuration, respectfully.
Figure 5B:
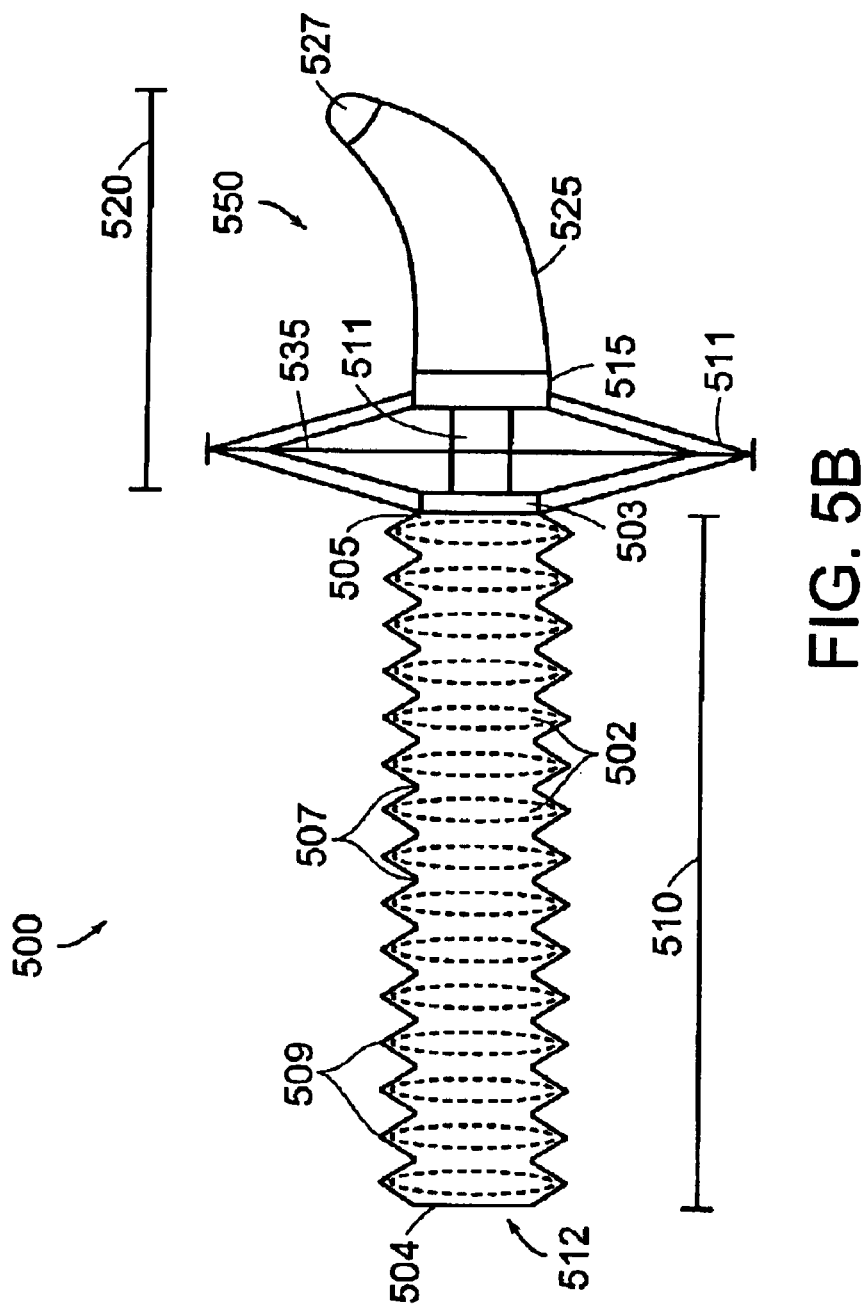
Figure 6:
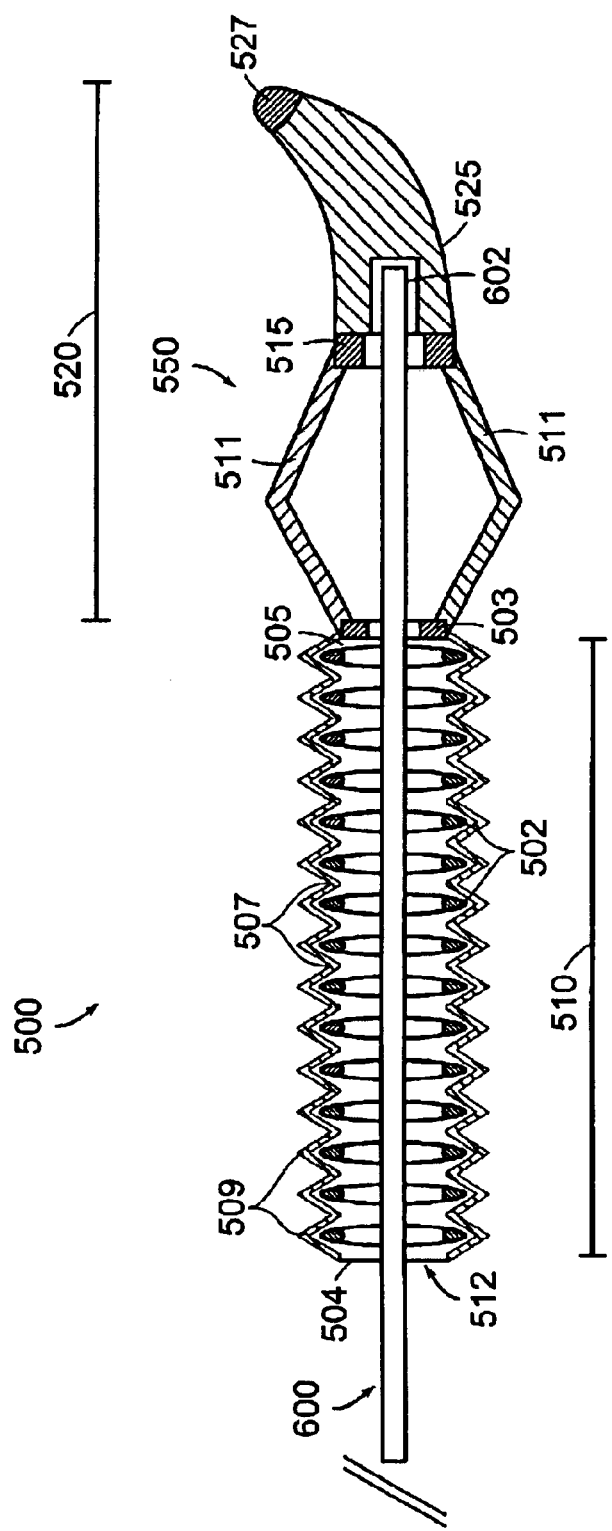
FIG. 6 is a schematic longitudinal cross-sectional view of the stent of FIGS. 5A and 5B with a stylet inserted therein.

FIGS. 5A and 5B are schematic representations of an alternative embodiment of a stent 500 including a distal region 520 with a malecot 550 and a curved end 525. The stent 500 is similar in construction to the stent 100 depicted in FIGS. 2–4. As shown in FIG. 5A, a distal end 505 of an elongated segment 510 is coupled to a proximal end 503 of a multi-winged malecot 550, which prevents the proximal migration of the stent 500. The malecot 550 includes wings 511 and a distal end 515. In this embodiment a four-winged malecot 550 is depicted; however, other embodiments could have two or more wings 511 to prevent the proximal migration of the stent 500. The malecot 550 also includes an orifice 508, which is in fluid communication with a lumen 512. In operation, at least some urine enters the stent 500 through the orifice 508 and flows proximally down the prostatic urethra 7.

The malecot 550 has at least two distinct configurations; an extended configuration and a collapsed configuration. FIG. 5A shows the stent 500 with the wings 511 of the malecot 550 in a substantially collapsed configuration. To achieve the collapsed configuration, the medical professional extends the distal end 515 of the malecot 550 along the longitudinal axis 530 of the elongated segment 510. This may be carried out using a pushing device or stylet 600 (see FIG. 6) while inserting the stent 500 into the body of a patient. Generally, the malecot 550 is in the collapsed configuration during insertion so as not to injure the patient's urethra 3. In FIG. 5B, the wings 511 of the malecot 550 are in the extended configuration. To prevent the distal region 520 from migrating out of the bladder 2, the outside diameter 535 of the malecot 550 in the extended configuration is greater than the diameter of the prostatic urethra 7. In one embodiment, the malecot 550 is biased in the extended configuration and, therefore, will return to this configuration in the absence of external compressive forces acting upon it. Once the malecot 550 is positioned in the bladder 2, the wings 511 assume the extended configuration, thus preventing proximal migration down the prostatic urethra 7.

The distal region 520 of the stent 500 may include a curved end 525 to assist the medical professional when inserting the stent 500 through the curved sections of the patient's urethra 3 (See FIG. 1). In addition, a small amount of metal or other radiopaque material, such as, for example, bismuth, may be embedded within a distal tip 527 of the curved end 525, thereby enabling the physician to confirm the proper placement of the stent 500 by radiographic techniques. In an alternative embodiment, the stent 500 can further include a proximal retention structure (not shown) disposed on the proximal end 504.

Attachment of the distal region 520 to the elongated segment 510 may be carried out using biocompatible adhesives or bonding techniques. Bonding of the components may be performed by heat bonding. Heat bonding functions by partially melting the material, allowing the melted material to adhere to a contacting surface or other component, and allowing the material to cool and harden, thus forming a bond. Heat bonding methods include radio frequency bonding, induction heating, and conduction heating. The material of a first component may be selected to melt at a similar temperature as a second component so that both components are melted during the heat bonding process. Alternatively, either the first or second component may be constructed from a material with a lower melting temperature than the other component in order that only the component with the lower melting temperature may melt during the bonding process.

Alternatively, the distal region 520 may be bonded by the use of a solvent, such as cyclohexanone and/or methylethylketone. Alternatively, a silicone adhesive may be used. The solvent acts by dissolving and swelling the material of the components. As the materials dissolve and swell, the components adhere to each other. The solvent is then removed allowing for the dissolved and swollen materials to harden and thus complete the bonding process. Alternatively, the distal region 520 and/or retention structures may be integrally formed with the elongated segment 510.

The prostatic stent 500 may be inserted into the body of a patient using a pushing device or stylet 600. Prior to inserting the stent 500 into the patient, the stylet 600 is loaded into the lumen 512 of the stent 500 through a proximal end 504 of the elongated segment 510. As shown in FIG. 6, the stylet 600 is passed through the lumen 512 until the distal end 602 of the stylet 600 contacts and pushes against the curved end 525, causing the malecot 550 to assume the collapsed configuration. Referring to FIGS. 1 and 6, a medical professional inserts the curved tip 525 into the patient's meatus 5 and advances the stent 500 into the urethra 3 by applying force to the stylet 600. Using radiographic techniques, the medial professional monitors the location of the stent 500. When properly placed, the elongated segment 510 is positioned substantially within the prostatic urethra 7 of the patient and the distal region 520 is located in the bladder 2. Subsequently, the medical professional retracts the stylet 600 from the patient's urinary system. As a result, the malecot 550 assumes an extended configuration, thus preventing proximal migration of the stent 500. In one embodiment, the hoop 502 closest to the malecot 550 is especially radiopaque, thus allowing the physician to properly position the distal region 520 within the bladder 2 prior to deploying the malecot 500.

Figure 7A:
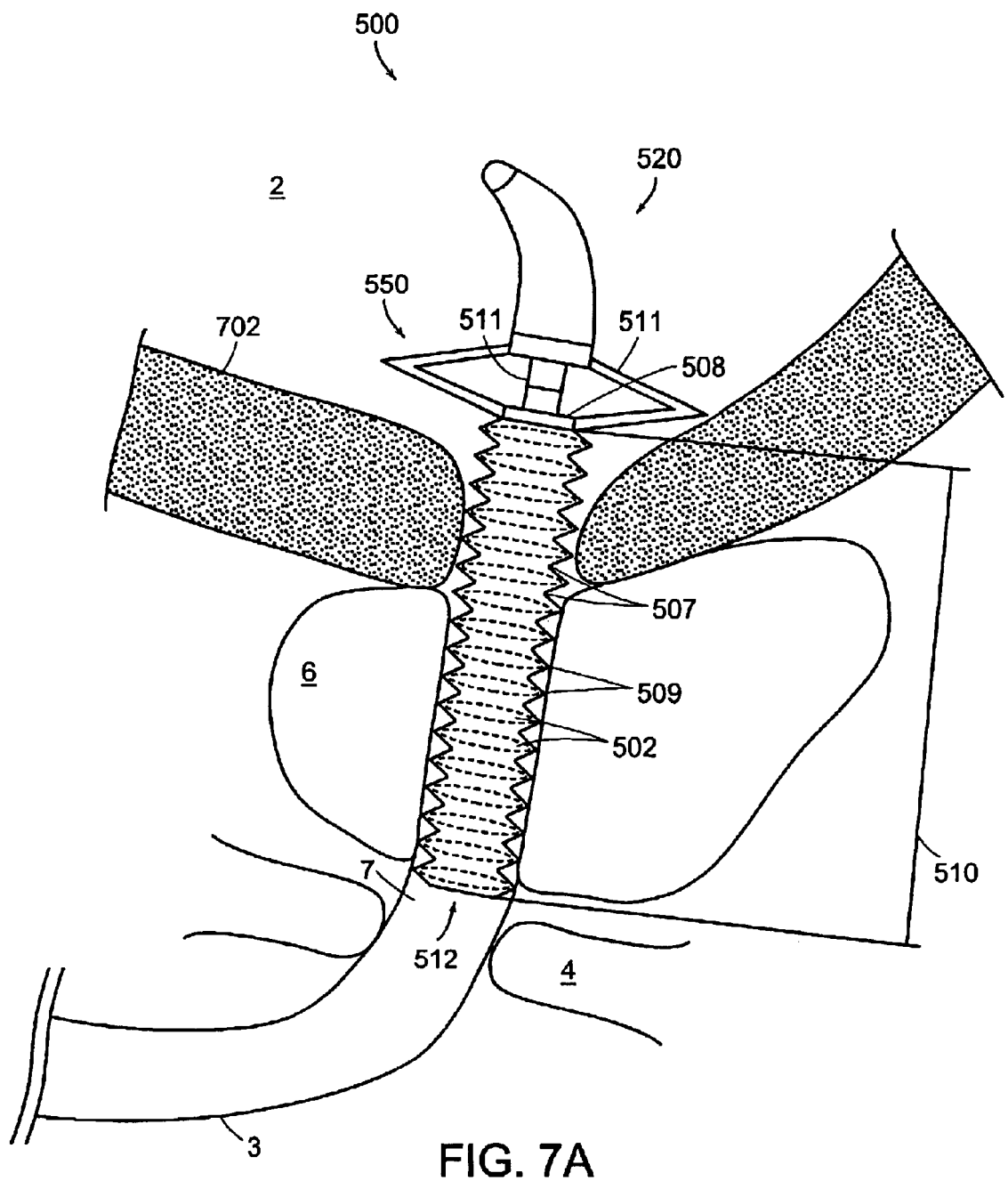
FIGS. 7A and 7B are schematic side views of the stent of FIGS. 5A and 5B placed within a prostatic urethra of a patient showing the transition from a longitudinally collapsed state to a longitudinally expanded state, respectively, in response to prostatic swelling.
Figure 7B:
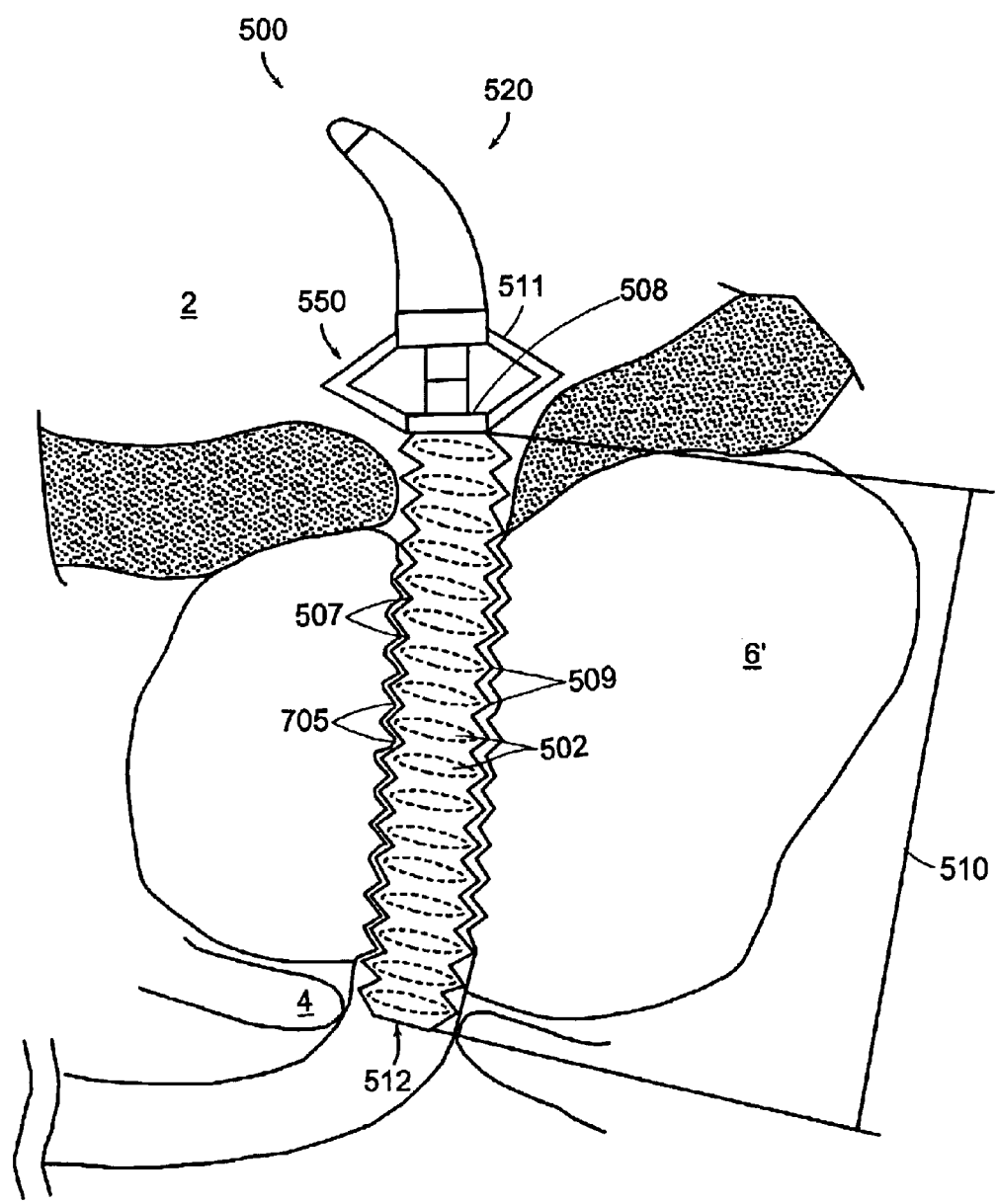

FIGS. 7A and 7B illustrate the stent 500 positioned within the prostatic urethra 7 of a patient with a normal prostate 6 and an enlarged prostate 6', respectively. FIG. 7A depicts the malecot 550 in the extended configuration, which prevents the distal region 520 of the stent 500 from migrating out of the bladder 2. The elongated segment 510 is positioned substantially within the prostatic urethra 7 and is shown in the compact configuration. In operation, the stent 500 receives at least some urine through the orifice 508 and into the lumen 512 of the elongated segment 510. The received urine flows through the lumen 512 until reaching the proximal end 504, where it empties into the patient's urethra 3.

FIG. 7B depicts the stent 500 within a prostatic urethra 7 surrounded by an enlarged prostate 6'. The elongated segment 510 is shown in an expanded configuration, illustrating how the elongated segment 510 accommodates anatomical changes due to prostatic swelling. The shape of the elongated segment 510 inhibits migration through the prostatic urethra 7 during prostatic swelling. Ridges 509 distributed along the elongated segment 510 engage adjacent tissue 705, especially during prostatic swelling. Specifically, lateral pressure exerted by the enlarged prostate 6' causes adjacent tissue 705 to embrace the ridges 509, thus frictionally engaging the elongated segment 510 and inhibiting migration through the prostatic urethra 7. At the same time, hoops 502 provide support to prevent the prostatic urethra 7 from collapsing, thus maintaining the flow of urine out of the bladder 2 and into the urethra 3.

The longitudinal expandability of the elongated segment 510 accommodates the anatomical changes associated with prostatic swelling and prevents occlusion of the stent 500. As the prostate 6' expands in a direction substantially parallel to the elongated segment 510, the frictionally engaged tissue 705 spreads apart the ridges 509 causing hinged members 507 to assume an open configuration. As a result, the elongated segment 510 expands commensurately with the adjacent prostatic tissue 6'.

Longitudinal expansion is also useful where severe prostatic swelling may push the bladder wall 702 upward risking occlusion of the opening 508. As shown in FIG. 7A, the expanding elongated segment 510 advances the distal region 520 further into the bladder 2, thus preventing the bladder wall 702 from surrounding the distal region 520. As a result, urine contained in the bladder continues to have access to the opening 508 even under conditions of severe prostatic swelling. As the patient's condition improves, the prostate 6' decreases in size. Because the plurality of hinged members 507 can be biased in a compacted state, the elongated segment 510 reduces in length as the prostate 6' reduces in size. Once in a compacted configuration, the elongated segment 510 is ready to re-extend in the event that prostatic swelling reoccurs. In addition, longitudinal expansion is particularly useful for minimizing patient discomfort due to compressive forces exerted on tissues lodged between the retention structure and the swelling prostate 6', such as, for example, the bladder wall 702. Discomfort is reduced by allowing the elongated segment 510 to expand commensurately with the swelling prostate 6' thus relieving the pressure exerted on the compressed tissues.

Having thus described certain embodiments of the present invention, various alterations, modifications, and improvements will be apparent to those of ordinary skill. Such alterations, modifications, and improvements are within the spirit and scope of the invention, and the foregoing description of certain embodiments is not exhaustive or limiting.

What is claimed is:

1. A stent for use in a prostatic urethra of a patient, comprising:
    an elongated segment comprising a first end, a second end, and a plurality of hoops defining a lumen therethrough;
    a flexible polymer material bridging the plurality of hoops to facilitate expansion of the elongated segment during prostatic swelling when the stent is within the prostatic urethra of the patient;
    a first malecot comprising a proximal end and a distal end, the proximal end of the first malecot being disposed at the first end of the elongated segment; and
    a curved tip disposed at the distal end of the first malecot.

2. The stent of claim 1 further comprising a second malecot disposed at the second end of the elongated segment.

3. The stent of claim 1 wherein each of the plurality of hoops comprises a wire.

4. The stent of claim 3 wherein at least one of the wires comprises a biocompatible material, which comprises stainless steel, titanium, a nickel-titanium alloy, or a polymer.

5. The stent of claim 1 wherein each of the hoops is spaced apart from at least one other of the hoops.

6. The stent of claim 1 wherein the flexible polymer material comprises a low durometer silicone.

7. The stent of claim 1 wherein the flexible polymer material is resilient.

* * * * *